United States Patent [19]
Buelna

[11] Patent Number: 5,209,749
[45] Date of Patent: May 11, 1993

[54] FLUOROSCOPICALLY ALIGNABLE CUTTER ASSEMBLY AND METHOD OF USING THE SAME

[75] Inventor: Terrence J. Buelna, Rancho Santa Margarita, Calif.

[73] Assignee: Applied Urology Inc., Laguna Hills, Calif.

[21] Appl. No.: 824,897

[22] Filed: Jan. 22, 1992

Related U.S. Application Data

[63] Continuation of Ser. No. 522,240, May 11, 1990, abandoned.

[51] Int. Cl.⁵ .............................................. A61B 17/39
[52] U.S. Cl. .................................... 606/45; 606/159; 128/658
[58] Field of Search ................. 606/194, 159, 45, 167; 604/22; 128/656, 657, 658, 654

[56] References Cited

U.S. PATENT DOCUMENTS

| | | | |
|---|---|---|---|
| 3,605,750 | 9/1971 | Sheridan et al. ...................... | 128/658 |
| 3,847,157 | 11/1974 | Caillouette et al. ............. | 128/656 X |
| 4,273,128 | 6/1981 | Lary ...................................... | 606/159 |
| 4,657,024 | 4/1987 | Coneys ................................. | 128/658 |
| 4,671,291 | 6/1987 | Wilson ................................. | 128/658 |
| 4,685,458 | 8/1987 | Leckrone ......................... | 606/159 X |
| 4,794,359 | 12/1988 | Sharrow ............................... | 128/658 |
| 4,796,637 | 1/1989 | Mascuch et al. .................... | 128/658 |
| 4,807,626 | 2/1989 | McGirr ........................... | 128/658 X |

Primary Examiner—Michael H. Thaler
Attorney, Agent, or Firm—Richard L. Myers

[57] ABSTRACT

A fluoroscopically alignable assembly is set forth. A longitudinally extending element support is extendable into a body cavity. The element, which may be in the nature of a cutting element, is supported by the element support. A radiopaque marker pattern is carried by the support. The pattern is such that by fluoroscopic viewing of the pattern, the user can determine the angular orientation of the element. In accordance with the method of the invention, the element can be aligned in a desired direction by fluoroscopically observing the marker pattern.

32 Claims, 2 Drawing Sheets

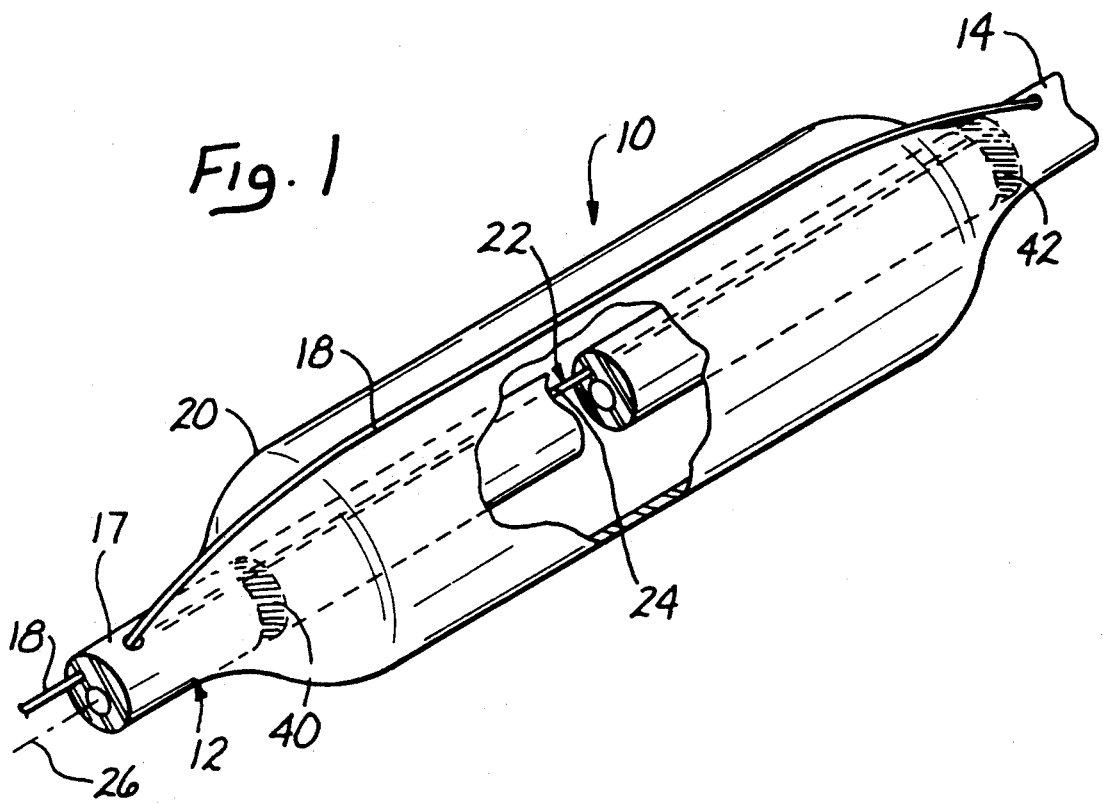
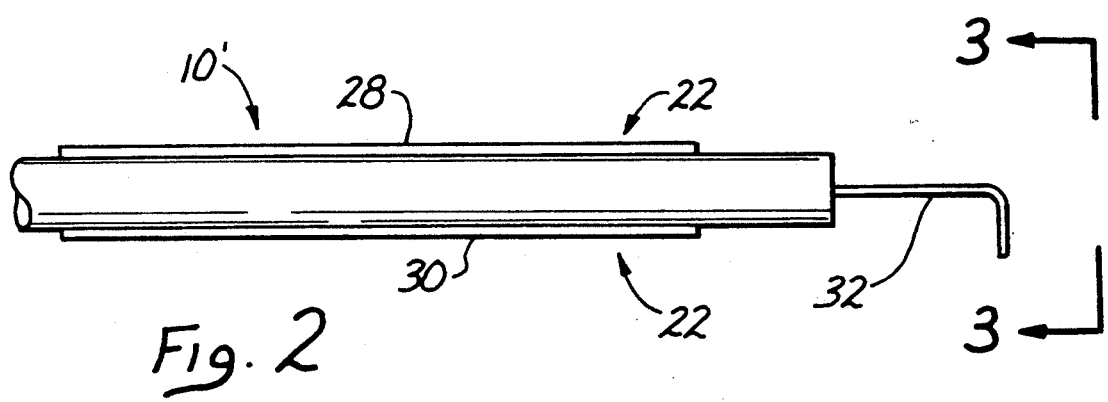
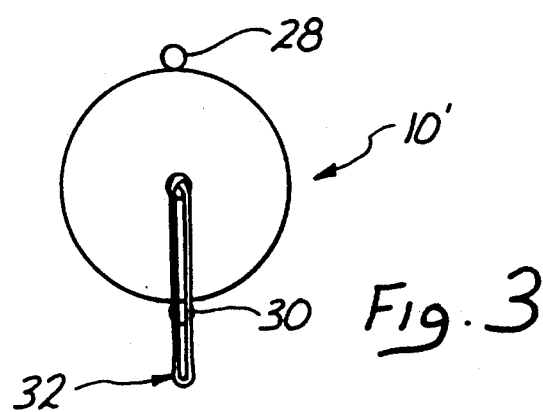

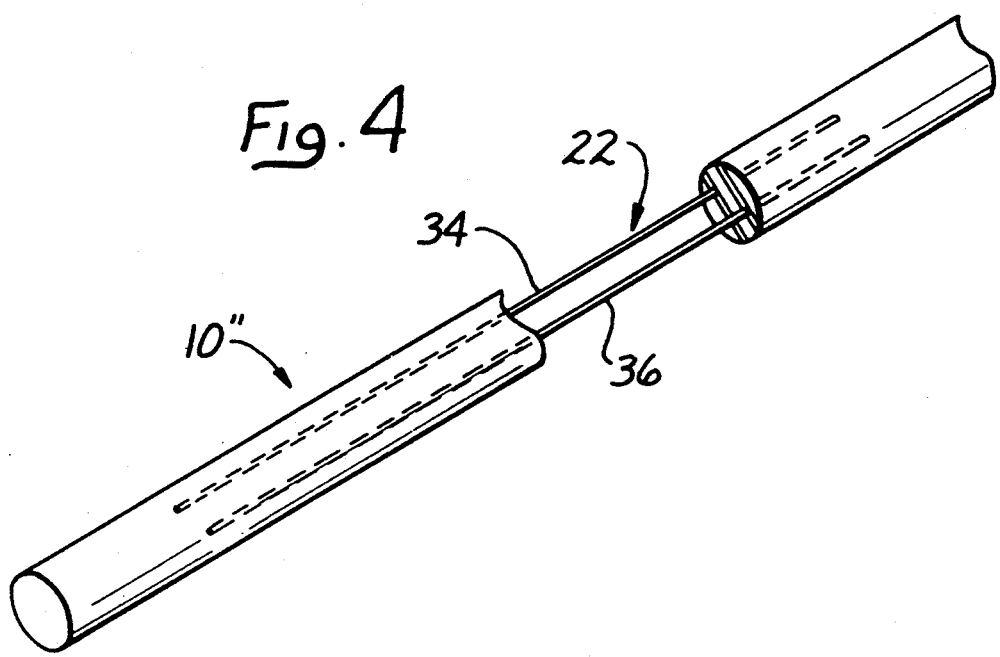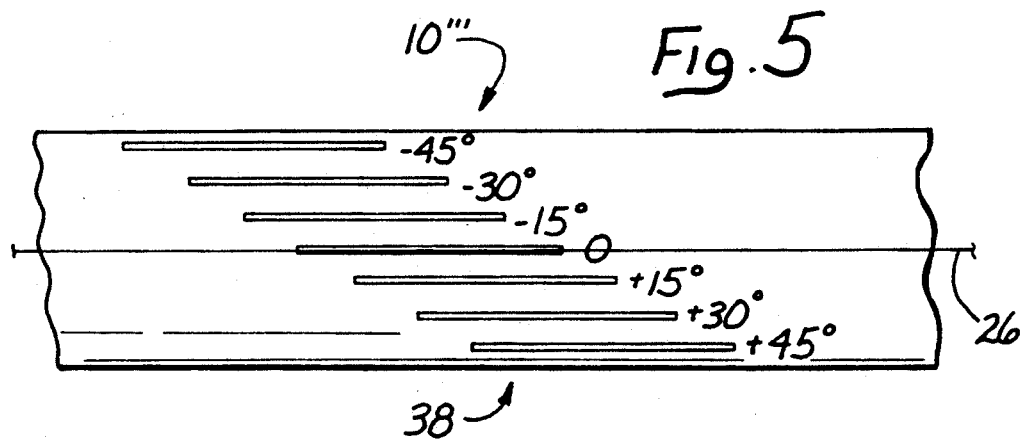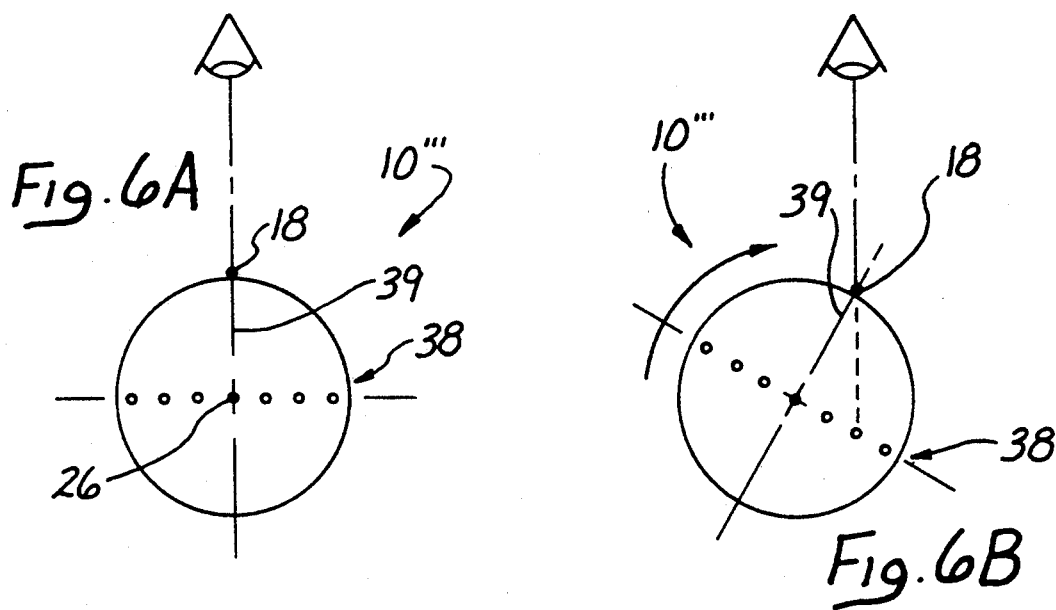

FLUOROSCOPICALLY ALIGNABLE CUTTER ASSEMBLY AND METHOD OF USING THE SAME

This is a continuation of application Ser. No. 522,240, filed May 11, 1990, now abandoned.

TECHNICAL FIELD

The present invention relates to an assembly, generally a cutter assembly, more specifically to a fluoroscopically alignable cutter assembly, of the type that is insertable in a body vessel, orifice or conduit such as the urethra.

BACKGROUND OF THE INVENTION

Catheters are used to insert cutting elements in body vessels, orifices, or conduits, such as arteries narrowed by atherosclerotic plaque and/or fibromuscular disease or to perform surgery within a constricted or obstructed ureter or urethra. Often, such catheters are of a dilation nature and serve to dilate the body vessels, orifices, and conduits. They basically consist of an elongated catheter, having an inflatable balloon or bladder at or near its distal end. A guide wire or other axial support means is often included to improve the torque control or "steerability" of the apparatus.

When a cutter assembly is inserted in the body vessel, orifice, or conduit, the cutting element carried by the cutting assembly must be properly aligned so that the cut made into the tissue or plaque is properly oriented. This is particularly important when the cutting element is carried by a dilation catheter and when the tissue is stressed and thereby subjected to significant trauma as it is cut by the cutting element. It would be highly undesirable if a cut was propagated in an undesirable direction since this might cause significant nerve and/or muscle damage. Fluoroscopy can be used to observe the cutter assembly as it is inserted into the patient. However, in many instances, for example, in prostate surgery, the fluoroscopic picture is a picture which looks downwardly upon the cutter assembly and the generally radiopaque cutting element, but does not readily show the precise orientation of the cutting element. Basically the cutting element shows up as a thin line under fluoroscopy and the precise orientation of the thin line is not readily apparent.

Radiopaque markings have been used to indicate the longitudinal positioning of balloons in body conduits. However, they have not been used to indicate angular orientation of such balloons (since balloons are generally radially symmetrical) nor have such markings been used to angularly orient cutters or the like in body conduits.

While the present invention is primarily contemplated as being useful with cutting elements it should be realized that it is more broadly useful with any device which is insertable in the body and which does not operate symmetrically but is instead sensitive to angular alignment about its longitudinal axis.

The present invention is directed to overcoming one or more of the problems as set forth above.

DISCLOSURE OF INVENTION

In accordance with an embodiment of the present invention, a fluoroscopically alignable assembly is set forth. The assembly comprises a longitudinally extending support having distal and proximal end portions and a longitudinal axis and being extendable into a body cavity. A radiopaque element is supported by the support in such a manner that rotation of the support about the axis changes the orientation of the element relative to the support. A radiopaque marker pattern is carried by the support, the pattern being such that by fluoroscopic viewing of the pattern a user can determine the orientation of the element about the axis.

In accordance with another embodiment of the present invention, a method is set forth of fluoroscopically aligning an assembly. The assembly, which is as set forth above, is inserted into a body vessel, orifice, or conduit. A fluoroscopic image of the assembly is detected. The position of the cutting is adjusted relative to the radiopaque marker pattern so as to align the element in a desired orientation for incising the body vessel, orifice, or conduit.

In accordance with still another embodiment of the invention tissue defining a body cavity is incised in a desired rotational orientation or orientations by aligning a cutting element as set forth above and then performing the incising.

The present invention allows one to readily align an element, for example, a cutting element, which is within a body vessel, orifice, or conduit whereby the cutting occurs in a desired direction. In accordance with an embodiment of the present invention, the length of the cutting element is also made visible due to the radiopaque marker pattern whereby both the angular orientation and the longitudinal position of cutting within the body vessel, orifice, or conduit can be readily controlled by the surgeon.

BRIEF DESCRIPTION OF THE DRAWINGS

The invention will be better understood by reference to the figures of the drawings wherein like numbers denote like parts throughout and wherein:

FIG. 1 is a partial perspective view of a cutter assembly in accordance with an embodiment of the present invention;

FIG. 2 is a side elevation view of an alternative embodiment of the cutter assembly in accordance with an alternate embodiment of the present invention;

FIG. 3 is a section view taken along the line 3—3 of FIG. 2;

FIG. 4 is a view similar to FIG. 1, showing an alternate embodiment in accordance with the present invention;

FIG. 5 is a partial top elevation view of a section of a cutter assembly in accordance with yet another embodiment of the present invention; and FIG. 6A is a radial view of the cutter assembly in FIG. 5, showing one step in an alignment procedure of the present invention; and

BEST MODE FOR CARRYING OUT INVENTION

Adverting to FIG. 1, a fluoroscopically alignable assembly, in the embodiment illustrated a cutter assembly 10, is shown which is in accordance with an embodiment of the present invention. The assembly 10 includes a longitudinally extending cutting element support 12, having a distal end portion 14 and a proximal end portion 17 and being extendable into a body cavity, orifice or conduit (not shown). A cutting element 18, which is generally itself radiopaque, is supported by the cutting element support 12. In the particular embodiment of FIG. 1, a balloon or bladder 20 is supported by the cutting element support 12 and the cutting element 18 is supported by the balloon 20. Such an assembly is described in more detail in co-pending applications, Ser. Nos. 07/522,254, now U.S. Pat. No. 5,080,660, filed concurrently herewith, and 07/298,477, filed Jan. 18, 1989, now abandoned and the disclosures therein are incorporated herein by reference thereto. A number of cutting elements 18 can be utilized in accordance with the present invention. However, the present invention is particularly useful when the cutting element is of the nature of a radio frequency electrosurgical cutting wire of the type described in the aforementioned co-pending U.S. patent applications.

In monopolar electrosurgical cutting a current is allowed to pass from an active cutting electrode through a patient's tissue and into a grounding pad or cable. The current cuts tissue at the active cutting electrode, the cutting rate being dependant on current density through the tissue in that area. At low current density heat is generated but no cut is achieved. At high current density fast cutting occurs.

In bipolar electrosurgical cutting the current passes from the active cutting electrode through the patient's tissue to a return electrode which is located in, or is in contact with, the patient's tissue a short distance away from the cutting electrode. The cutting and return electrodes are generally carried by a single instrument.

Current density depends on the current (measured in watts) applied and can be controlled utilizing an adjustment present on a conventional generator designed for this purpose. The current density also depends on the series impedance of the overall circuit. Series impedance is equivalent to the sum total of the resistance to the current throughout the circuit. It is affected by the material and the design of the active electrode, by the patient, by the type of tissue to be cut, and by the condition of contact established between the patient and (when a monopolar electrode is utilized) the grounding pad as well as by the location of the grounding pad relative to the cutting site. During surgery, the generator setting is usually adjusted to compensate for this variability and to reflect the surgeon's preference. Generators used in this type of surgery have a wide range of power output to accommodate a variety of procedures and devices.

The objective in electrosurgical cutting is to heat the tissues cells so rapidly that they explode into steam leaving a cavity in the cell matrix. The heat is meant to be dissipated in the steam and to not conduct through the tissue to thereby dry out adjacent cells. When the electrode is moved and fresh tissue is contacted new cells are exploded and the incision is made. Such electrosurgical cutting involves the sparking of the current to the tissue. The current utilized is in the radio frequency range and operates by the radio frequency current jumping across an air gap to the tissue. This is known as sparking.

An explanation of electrosurgical cutting theory can be found in the FORCE 1 Instruction Manual published by Valleylab of Boulder, Colo. on Mar. 1, 1986. The entire text of the FORCE 1 Instruction Manual is incorporated herein by reference.

In accordance with the embodiment of FIG. 1, a radiopaque marker pattern 22 is provided and is carried by the cutting element support 12. The pattern 22 is such that by fluoroscopic viewing of the pattern 22 (and usually the cutting element 18, as well), a user can determine the angular orientation of the cutting element 18 about its longitudinal axis 26. In the particular embodiment illustrated, the pattern 22 is in the nature of a radiopaque wire 24 which fits in a passage in the cutting element support 12. If one looks downwardly upon the cutting element 18, and aligns the cutting element 18 with the wire 24 so that only a single line is apparent to the surgeon, then the cutting element 18 is aligned to out directly upwardly (the possibility of a 180° misalignment is avoidable since the cutter assembly 10 can be inserted with sufficient care so that it is less than 90° out of alignment) from the longitudinally extending cutting element support 12. Also, the assembly 10 can have markers on its proximal (out-of-body) end to allow positioning within 45° of the desired target orientation. If the cutter assembly 10 is otherwise aligned, for example if it is rotated some number of degrees about the illustrated axis 26, then the surgeon will see two lines in the fluoroscopic picture, one corresponding to the cutting element 18 and the other to the wire 24 (one or more of the lines forming the radiopaque pattern 22 can be made distinguishable from the line representative of the cutter element 18, for example, the pattern lines can be dashed lines, have transverse dashes across them, or the like). The surgeon can then rotate the cutter assembly 10 about the axis 26 until the two visible lines coincide to properly position the cutting element 18 directly above the wire 24.

Generally the radiopaque marker pattern 22 is made up of lines which are relatively thin. In particular, such lines, whether they are made up of wires or are in the nature of radiopaque inks, are no greater in extension (diameter in the case of wires) than is the cutting element 18 itself. If the lines which make up the marker pattern 22 are significantly wider than the cutting element 18 there is an alignment error results since the cutting element 18 can be misaligned at any location opposite the width of the potentially wider lines of the marker pattern 22. Thus, it is preferred that the Width of the lines of the marker pattern 22 be no greater than the width of the cutting element 18.

FIGS. 2 and 3 show an embodiment of the invention wherein the marker pattern 22 comprises two radiopaque markers 28 and 30, each parallel to and extending along the support 12 and each being on the same diameter as seen in FIG. 3. When the surgeon is viewing the cutter assembly 10, of FIGS. 2 and 3 from above, the radiopaque markers 28 and 30 can be aligned to appear to be only a single line, thus assuring proper orientation of, for example, a cutting loop 32, which extends from the distal end portion 14 of the cutting element support 12.

FIG. 4 illustrates an embodiment of a cutter assembly 10" very much like that of FIG. 3, but wherein the radiopaque marker pattern 22 is in the nature of two wires 34 and 36, both within appropriate passages in the cutting element support 12. A cutting element is not shown but, if present, would extend from the distal end portion of the cutting element support 12. This embodiment is also useful if the element being aligned is not a cutting element and is not itself radiopaque.

FIGS. 5 and 6A and 6B illustrate an embodiment of the present invention wherein the cutter assembly 10"' serves for orientating the cutting element 18 at a desired angle relative to the axis 26. In the embodiment illustrated in FIGS. 5 and 6, there are a plurality of radiopaque indicator lines 38 carried by (in the embodiment illustrated within) the cutting element support 12 and each of the radiopaque indicator lines 38 is laterally removed from a line 39 defined by the intersection of a plane defined by the axis 26 and by the cutting element 18, which is otherwise in the nature shown in FIG. 1. Each of the radiopaque indicator lines 38 is a different distance from this intersection line in order to allow selective angular orientation of the cutting element 18 while it is within a body vessel, cavity, or conduit. For example, the cutting element support 12 can be rotated until the cutting element 18 appears to be over any one of the opaque indicator lines 38, which can be in the nature of radiopaque lines or can be imbedded wires, whereby a cut may be made at a desired orientation about the axis 26. FIGS. 6A and 6B illustrate the alignment procedure.

Also in accordance with the present invention, and adverting particularly to FIG. 1, it is possible to provide additional radiopaque markers 40 and 42, one of which is each end of the cutting element 18. In this way, the surgeon can observe not only the radial direction in which the cutting element 18 is going to proceed on inflating of the balloon 20, but also just where along a body conduit the cutting element 18 is going to cut into the particular body conduit.

In accordance with the method of the invention, the alignable cutter assembly 10, 10', 10'', or 10''', is inserted in a body vessel, cavity, or conduit to the desired depth. Fluoroscopic images are obtained of the cutter assembly 10, 10', 10'', or 10''', within the body. The cutting element 18 is then aligned in a desired angular orientation relative to the axis 26 using the radiopaque marker pattern 22. The precise depth within the body can also be adjusted by observing the radiopaque markers 40 and 42, when present. Thereafter, incising is carried out in the desired direction. If desired, the element can be reoriented in a different angular orientation and an additional incision can be made.

INDUSTRIAL APPLICABILITY

The present invention provides a cutter assembly 10 which allows a cutting element 18 to be aligned properly within a body vessel, cavity, or conduit so as to provide an incision in a desired direction.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method of aligning an assembly in a selected orientation with respect to tissue defining a body vessel, orifice, conduit, or other body cavity, comprising the steps of:

inserting a longitudinally extending support having a distal end portion, a proximal end portion and a longitudinal axis, into the body cavity, said support carrying an active element in such a manner that rotation of said support about said axis changes the orientation of said element relative to said body cavity, said support having a radiopaque marker pattern, said pattern being such that by fluoroscopic viewing of said pattern a user can determine the orientation of said element relative to said body cavity;

rotating the active element and the marker pattern circumferentially of the axis, the marker pattern exhibiting a different visual characteristic for each angular orientation of the active element relative to the tissue;

during the rotating step observing the different visual characteristics of the marker pattern, including a known visual characteristic associated with a preferred angular disposition of the active element relative to the tissue;

ceasing rotation of the support in response to observation of the known visual characteristic; and activating said active element when the active element is in the preferred angular disposition.

2. A method as set forth in claim 1, wherein said element extends longitudinally along said support and wherein said marker pattern includes a radiopaque line running along said support generally parallel to said element.

3. A method as set forth in claim 2, wherein said marker pattern further includes at least one radiopaque indicator line on said support laterally removed from said radiopaque line.

4. A method as set forth in claim 2, wherein said marker pattern further includes a plurality of radiopaque indicator lines extending along said support, each laterally removed from said radiopaque line a different distance to allow selective angular alignment of said element within a body conduit.

5. A method as set forth in claim 4, wherein said element extends longitudinally along said support and the method further comprises the step of:

aligning said element longitudinally by observation of said marker pattern.

6. A method as set forth in claim 1, wherein said element is radiopaque.

7. A method recited in claim 1 wherein the rotating step includes the step of rotating the support.

8. A method recited in claim 1 wherein the active element is a cutter and the activating step includes the step of energizing the cutter to cut the tissue and enlarge the body cavity.

9. The method recited in claim 1 wherein the observing step includes the step of fluoroscopically viewing the visual characteristics of the rotating marker pattern.

10. A method of producing a controlled incision at a desired angular orientation with respect to tissue defining a vessel, orifice, conduit, or other body cavity, comprising:

inserting a longitudinally extending support having a distal end portion, a proximal end portion and a longitudinal axis, distal end portion first, into said body cavity, said support carrying a radiopaque marker pattern including a plurality of indicators each having a visual characteristic different than the other indicators and each alignable with respect to the cutting element to indicate a known orientation of the cutting element relative to the body cavity, the marker pattern facilitating visual orientation of said cutting element relative to the body cavity, the marker pattern facilitating visual orientation of said cutting element in a preferred angular disposition relative to said tissue;

rotating the support to move the cutting element circumferentially of the axis, and to bring a different one of the indicators into alignment with the cutting element thereby exhibiting a different visual characteristic for each angular disposition of the element relative to the tissue;

during the rotating step observing the different visual characteristics being exhibited by the marker pattern, including a known visual characteristic associated with a preferred angular disposition of the cutting element relative to the tissue;

ceasing rotation of the cutting element in response to observation of the known visual characteristic; and activating said cutting element to cut the tissue when the cutting element is in the preferred angular disposition.

11. A method as set forth in claim 10, herein said element extends longitudinally along said support and wherein said marker pattern includes a radiopaque line running along said support generally parallel to said element.

12. A method as set forth in claim 11, wherein said marker pattern further includes at least one radiopaque indicator on said support laterally removed from said radiopaque line.

13. A method as set forth in claim 12, wherein said marker pattern further includes a plurality of radiopaque indicators on said support, each laterally removed from said radiopaque line a different distance to allow selective angular alignment of said element within the body cavity.

14. A method as set forth in claim 10, wherein said cutting element is radiopaque.

15. The method recited in claim 10 wherein the cutting element is an electrosurgical wire and the energizing step includes the step of introducing a radio frequency current to the wire to enlarge the body cavity.

16. A fluoroscopically alignable assembly adapted for insertion into an orifice, vessel, conduit, or other body cavity, comprising:

a support member having an axis extending between a proximal end and a distal end of the support member, at least the distal end being adapted for insertion into the body cavity;

a radiopaque cutting element carried by the support member and movable with the support member such that rotation of the support member about the axis moves the element into different angular orientations with respect to the body cavity, the cutting element having a predetermined width;

a plurality of indicia disposed on the support member and having a fixed relationship with the element, each of the indicia having a width which is not appreciably greater than the width of the cutting element and being individually fluoroscopically viewable as a different pattern associated with a known angular orientation of the cutting element, about the axis, relative to the body cavity; and means disposed at the proximal end of the support member for rotating the support member to angularly displace the cutting element and the indicia relative to the body cavity.

17. The assembly recited in claim 16 wherein the body cavity is defined by body tissue and the element is adapted to perform a function relative to the tissue at a preferred location disposed generally radially of the axis.

18. The assembly recited in claim 17 wherein the indicia includes at least a pair of radiopaque symbols which form the different patterns in response to rotation of the support member.

19. The assembly recited in claim 18 wherein the cutting element comprises one of the radiopaque symbols.

20. The assembly recited in claim 18 wherein the radiopaque symbols are lines extending along the support member and the patterns differ in the spacing of the lines as the support member is rotated.

21. The assembly recited in claim 18 wherein the indicia include a plurality of lines forming patterns such that a different one of the lines is alignable with the cutting element to indicate the desired orientation of the cutting element relative to the body cavity.

22. The assembly recited in claim 21 wherein the lines extend longitudinally and each of the lines is substantially parallel to the axis of the support member.

23. The assembly recited in claim 16 wherein the cutting element comprises a wire responsive to an electrical signal to cut the tissue along a particular plane.

24. The assembly recited in claim 23 wherein the axis is disposed in the particular plane.

25. A fluoroscopically alignable assembly adapted for operative disposition in a vessel, orifice, conduit or other body cavity, comprising:

an elongate support having a longitudinal axis extending between a distal end portion and a proximal end portion of the support, the support being rotatable about the axis when disposed in the body cavity;

a radiopaque cutting element having a predetermined width, the cutting element being carried by the distal end portion of the support about the axis such that rotation of the support moves the cutting element through a multiplicity of locations within the body cavity, the locations including a particular location associated with a desired angular orientation of the cutting element within the body cavity;

a radiopaque marker pattern, having a fixed relationship with the cutting element, the pattern including a plurality of indicators, each having a predetermined width which is not appreciably greater than the width of the cutting element and having a radiopaque characteristic which is different than the radiopaque characteristic of the other indicators, each indicator having properties for being oriented relative to the cutting element to present a visual characteristic representative of an associated one of the locations;

means disposed at the proximal end portion of the support for rotating the support to achieve the particular visual orientation; whereby the cutting element is disposed at the particular location associated with the desired angular relationship between the cutting element and the body cavity.

26. The assembly recited in claim 25 wherein the body cavity is defined by tissue and the cutting element comprises a wire adapted to receive an electrical signal for cutting the tissue.

27. The assembly recited in claim 26 wherein the wire extends longitudinally of the support member in a plane which extends generally radially of the axis.

28. The assembly recited in claim 25 wherein the cutting element extends longitudinally of the support in spaced relationship to the axis of the support.

29. The assembly recited in claim 25 wherein the cutting element forms part of the marker pattern.

30. The assembly recited in claim 25 wherein the indicators are disposed in a different angular relationship and a different longitudinal relationship with the active element.

31. The assembly recited in claim 30 wherein the indicators are disposed circumferentially about of the elongate support.

32. The assembly recited in claim 30 wherein the indicators are disposed in a common plane with the axis of the support.

* * * * *

UNITED STATES PATENT AND TRADEMARK OFFICE
CERTIFICATE OF CORRECTION

PATENT NO. : 5,209,749

DATED : May 11, 1993

INVENTOR(S) : Terrence J. Buelna

It is certified that error appears in the above—identified patent and that said Letters Patent is hereby corrected as shown below:

Col. 4, line 36 change "Width" to --width--.

Col. 4, line 44 change "10" to --10'--.

Col. 7, line 12 change "herein" to --wherein--.

Signed and Sealed this

Ninth Day of August, 1994

Attest:

BRUCE LEHMAN

Attesting Officer    Commissioner of Patents and Trademarks